(12) United States Patent
Mueller et al.

(10) Patent No.: US 9,260,354 B2
(45) Date of Patent: *Feb. 16, 2016

(54) DEVICE AND METHOD FOR THE PRODUCTION OF RADIOCHEMICAL COMPOUNDS

(71) Applicants: ABX ADVANCED BIOCHEMICAL COMPOUNDS GMBH, Radeberg (DE); GESIM-GESELLSCHAFT FUER SILIZIUM-MIKROSYSTEME MBH, Grosserkmannsdorf (DE)

(72) Inventors: Marco Mueller, Radeberg (DE); Steffen Howitz, Grosserkmannsdorf (DE)

(73) Assignees: ABX ADVANCED CHEMICAL COMPOUNDS GMBH, Radeberg (DE); GeSIM—Gesellschaft für Silizium-Mikrosysteme mbH, Grosserkmannsdorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/592,283

(22) Filed: Jan. 8, 2015

(65) Prior Publication Data
US 2015/0133650 A1    May 14, 2015

Related U.S. Application Data

(63) Continuation of application No. 13/806,019, filed as application No. PCT/DE2011/075143 on Jun. 20, 2011, now Pat. No. 8,980,184.

(30) Foreign Application Priority Data

Jun. 22, 2010   (DE) .......................... 10 2010 017 511

(51) Int. Cl.
*B01J 10/00*   (2006.01)
*C07B 59/00*   (2006.01)
(Continued)

(52) U.S. Cl.
CPC ............. *C07B 59/005* (2013.01); *B01J 19/004* (2013.01); *B01J 19/0046* (2013.01);
(Continued)

(58) Field of Classification Search
CPC ..... B01L 19/0046; B01L 19/08; B01L 19/12; B01L 19/126; B01L 2219/00141; B01L 2219/00691; G01N 35/10; G01N 35/1011; G01N 35/109; B01J 19/0046; B01J 19/08; B01J 19/12; B01J 19/126; B01J 2219/00141; B01J 2219/00691
USPC .................................. 422/129, 130, 501, 509
See application file for complete search history.

(56) References Cited

U.S. PATENT DOCUMENTS

| 5,433,120 | A  | * | 7/1995  | Boyd et al. ................. 73/863.81 |
| 2003/0232967 | A1 | * | 12/2003 | Chait et al. ..................... 530/350 |
| 2004/0022696 | A1 | * | 2/2004  | Zigler et al. .................. 422/159 |

FOREIGN PATENT DOCUMENTS

WO   WO 2008/000804   *   1/2008   .................... 422/130

*Primary Examiner* — Jill Warden
*Assistant Examiner* — Dwayne K Handy
(74) *Attorney, Agent, or Firm* — Maier & Maier, PLLC (57) ABSTRACT

The invention relates to a device for the preparation of radiochemical compounds. It is provided that the device comprises at least a reaction module, a dosing module, and a storage module, wherein
the reaction module has at least one reaction vessel having a closable opening through which substances needed for the preparation of a predetermined radiochemical compound can be introduced into the reaction vessel of the reaction module and through which the prepared radiochemical compound can be removed from the reaction vessel of the reaction module;
the dosing module has at least one pipetting head which can be moved relative to the storage module and the reaction module and in x, y, and z directions and also has at least one dosing unit; and
at least one reservoir for one of the substances needed for the preparation of the respective radiochemical compound is formed in the storage module.

9 Claims, 3 Drawing Sheets

(51) Int. Cl.
*B01J 19/00* (2006.01)
*C07H 5/02* (2006.01)

(52) U.S. Cl.
CPC ............ *B01J 19/0093* (2013.01); *C07B 59/00* (2013.01); *C07H 5/02* (2013.01); *B01J 2219/0004* (2013.01); *B01J 2219/00038* (2013.01); *B01J 2219/0072* (2013.01); *B01J 2219/0081* (2013.01); *B01J 2219/00094* (2013.01); *B01J 2219/00132* (2013.01); *B01J 2219/00141* (2013.01); *B01J 2219/00283* (2013.01); *B01J 2219/00333* (2013.01); *B01J 2219/00364* (2013.01); *B01J 2219/00585* (2013.01); *B01J 2219/00599* (2013.01); *B01J 2219/00704* (2013.01); *B01J 2219/00731* (2013.01); *B01J 2219/00788* (2013.01); *B01J 2219/00882* (2013.01); *B01J 2219/00889* (2013.01); *B01J 2219/00916* (2013.01); *B01J 2219/00941* (2013.01); *C07B 2200/05* (2013.01)

DEVICE AND METHOD FOR THE PRODUCTION OF RADIOCHEMICAL COMPOUNDS

The invention relates to a device for the preparation of radiochemical compounds, in particular of radiochemical medicinal drugs, a method for the preparation of the radiochemical compounds, a use of the device as well as a kit that can be used in the device.

In the medical diagnostics there are increasingly used short-lived, radio-labeled compounds, so-called radiotracers, the physiological and biochemical properties of which enable a non-invasive tomographic detection of metabolic processes in the human body. By using the modern tomographic method of positron emission tomography (PET) metabolic processes can be quantified by means of said radiotracers and the biodistribution of the radiodiagnostic agent can be detected from the outside. The tomographic detection of radiotracers, such as for example 2-desoxy-2-[$^{18}$F]fluoro-D-glucose ([$^{18}$F]-FDG), allows an early diagnosis of tumors which significantly differ with respect to the glucose metabolism of normal tissue. By the development of novel radiotracers on the basis of pharmacologically interesting compounds new possibilities of the non-invasive diagnostics of various clinical pictures have opened up in the last years.

The global share of the positron emission tomography (PET) in the overall market of diagnosis by means of imaging methods has explosively increased in the last years. Here, the largest share has the [$^{18}$F] fluoride as radioactive probe because in the form of the F-18 labeled sugar derivative ([$^{18}$F]-FDG) it visualizes by means of PET the exact localization of tumors down to the millimeters and enables an exact localization of the tumor extension. However, not only [$^{18}$F]-FDG FDG which is often referred to as the "workhorse" of nuclear medicine, but also further fluorinated tracers, e.g. for the diagnosis of neurological and cardiological diseases, have become increasingly important. Unfortunately, said tracers are only available to a few highly specialized hospitals with an own radiochemistry department. On the one hand, this is because of the short half-life periods of the 18F labeled tracers and on the other hand of the relatively large space required for the classic preparation of the radiotracers. So far, for the preparation of one PET tracer one requires a workplace shielded with lead plates (a so-called hot cell) the required space of which is about 2×3 m filling included. Hereby, total costs of more than 100,000 Euro are caused. Due to the size of the conventional modules multi-stage syntheses in the so-called "hot cells" can hardly be realized which means that many of the known and promising radiotracers are not even clinically used. Further limiting factors are the frequently long reaction times and costly purifying procedures with the conventional synthesis equipments.

For labeling radiotracers that can be used for positron emission tomography due to the pharmacokinetics only a few radionuclides come into consideration. For reasons of isotopic labeling at present in particular carbon-11 with a half-life of 20 min. and fluoro-18 with a half-life of 110 min. were preferred. The preparation of said radioactive nuclides is performed by means of a particle accelerator (cyclotron) which generates the desired radioactive nuclides by bombardment of protons or deuterons to specifically developed targets. As the target for the preparation of [$^{18}$F] fluoride there is used $^{18}$O enriched water ($H_2^{18}O$, O-18 water) which has a relatively high price due to its quite costly preparation by distillation from native water.

In general, the [$^{18}$F] fluoride prepared in the cyclotron is separated from the target water by ion exchange in which on the one hand losses of O-18 water are caused and on the other hand the water can be contaminated with organic substances by contacting the ion exchanger. Following azeotropic distillation in the subsequent synthesis step the [$^{18}$F] fluoride activated by means of phase transfer catalysts is reacted with the corresponding educt (precursor) in an organic solvent e.g., acetonitrile (labeling). All of the physico-chemical processes take place in synthesis modules which conditional on a number of reaction steps (e.g., ion exchange, distillation, drying, reaction) are provided with relatively complex control systems.

More novel developments are in particular adjusted to miniaturization and thus, to the use of microchips. An alternative to the separation of carrier-free [$^{18}$F] fluoride from target water and its radiochemical reaction are electrochemical flow cells. Separation of the radionuclide present as anion is achieved by electrofixation in a flow cell with permanent electrode arrangement under maintenance of an electrical field. Then, by pole changing and optionally an intermediate rinsing desorption of the radionuclide can take place. In doing so, costly distillations and drying steps, respectively, are avoided such that [$^{18}$F] fluoride can be converted into a chemically reactive form after anodic fixation by simply washing with an aprotic solvent. Based on this, there is made the carrier-poor $^{18}$F labeling into the desired radiotracer.

From WO 03/078358 A2 there is known a miniaturized device for the preparation of radio-labeled compounds. The device has a reaction chip with a surface of 1 cm$^2$ and possesses inlet ports for supplying reactants and outlet ports for draining off the reaction mixture or its components. A further port might for example be provided for introducing a deprotection agent. The inlet ports, outlet ports and the further ports are connected to each other via a system of micro-channels formed in the device. An analytical chip can be connected to the reaction chip which in addition to an inlet port connected to the outlet port of the reaction chip and an outlet port has two further ports for supplying or draining off, respectively, electrolyte buffer solutions. From the analytical chip the reaction mixture finally reaches a separation device in which then the desired radiotracer is obtained. The individual chips can also be realized in an individual device wherein in the individual device a number of micro-channels is provided.

US 2005/0232387 A1 discloses a system for synthesizing a radiochemical compound in a micro-fluidal milieu. The system comprises a micro reactor with several inlet ports, an outlet port, and a micro-channel connecting the inlet ports and the outlet port. The precursor and a solution containing the radioactive isotope are supplied via the inlet ports. Both substances contact each other in the micro-channel such that during passage of both substances through the micro-channel both substances react with each other to obtain the radiochemical compound. Then, at the outlet port the radiochemical compound leaves the micro reactor.

However, reaction in micro-channels is associated with a number of difficulties. On the one hand, micro-fluidics requires a careful coordination of the fluidics of the components in the channels, which often can only be accomplished with a lot of periphery (e.g. pumps, valves, heating and refrigeration units). It becomes even more problematic if then for different radiotracers different micro reactors have to be used. On the other hand, purification of the micro-channels involves a lot of effort. This avoids that different radiotracers can be prepared within a short time with the same microchip. Finally, the number of reaction stages that can be performed in the known micro reactors is limited. Each stage requires at least one inlet needing a micro-channel that is connected to the channel in which the precursor flows. As a rule, also further outlets are required for draining off waste products.

It is the object of the invention to eliminate the drawbacks of the prior art. In particular, there is provided a device for the preparation of radiochemical compounds, in particular radiochemical medicinal drugs such as radiotracers, which avoids long reaction times and costly purifying procedures required in the conventional synthesis equipments and offers high radiochemical yields and high flexibility with respect to the preparation of different radiotracers. Moreover, a method for the preparation of radiochemical compounds by means of said device as well as uses of said device are provided.

This object is solved by the features of claims 1, 10, 15, and 16. Practical developments of the invention result from the features of claims 2 to 9 and 11 to 14.

In accordance to the invention a device for the preparation of radiochemical compounds is provided which comprises at least a reaction module, a dosing module, and a storage module wherein
- the reaction module has at least one reaction vessel having a closable opening through which the substances needed for the preparation of a predetermined radiochemical compound are introduced into the reaction vessel and through which the prepared radiochemical compound is removed from the reaction vessel;
- the dosing module has at least one pipetting head which can be moved relative to the storage module and the reaction module and in x, y, and z directions and has at least one dosing unit; and
- at least one reservoir for one of the substances needed for the preparation of the respective radiochemical compound is formed in the storage module.

Preferably, a washing station for the dosing units is provided.

Preferably, the device is controlled by a control unit that is suitably formed in the dosing module and can be controlled with a software.

Moreover, the device can comprise a purifying module for separating the prepared radiochemical compound from the reaction mixture. The purifying module can comprise cartridges customary in radiochemistry, in particular chromatographic columns, and/or other purification means, such as for example high-pressure liquid chromatography (HPLC). Alternatively or additionally, the cartridges and/or other purification means required for the separation of the prepared radiochemical compound from the reaction mixture can also be integrated into the storage module. The latter is in particular advantageous when the storage module is provided as a kit.

In addition, the device can have a dispensing module in which the radiochemical compound purified in the purifying module is laced with an aqueous injection solution, e.g. an isotonic sodium chloride solution to obtain ready-made preparations. The dispensing module can comprise several vials into which the purified radiochemical compound can be filled at an each predetermined dose. Thus, the device according to the invention allows the preparation and dosage of a radiochemical compound which avoids the employment of a separate synthesis device and a separate dosing device required so far. Considering the costs of known dosing devices this is a further significant advantage of the invention.

In the following, a substance required for the preparation of the respective radiochemical compound is also referred to as "required substance". The term "required substance" comprises the starting materials needed for the preparation of a predetermined radiochemical compound, for example a precursor compound. It can also comprise the needed catalysts and purifying substances, such as solvents.

Preferably, each of the reaction vessels of the reaction module has an internal volume of 1 $\mu$l to 20,000 $\mu$l, more preferably 1 $\mu$l to 5,000 $\mu$l, even more preferably 1 $\mu$l to 2500 $\mu$l, and most preferably 1000 $\mu$l to 2000 $\mu$l. The reaction vessel can be a vial. Each reaction module has at least one reaction vessel, preferably 1 to 50 reaction vessels, particularly preferable 1 to 10 reaction vessels.

Each reaction vessel has an opening through which the substances needed for the preparation of the respective radiochemical compound can be introduced into the reaction vessel and through which the prepared radiochemical compound can be removed from the reaction vessel. Moreover, also gases can be introduced and/or drained off through the opening. Finally, the opening can also be used to generate overpressure or underpressure (vacuum) in the reaction vessel.

If several reaction modules are provided several radiochemical compounds can be prepared in parallel with only one device according to the invention. Even though only one reaction module is provided it is possible to quickly change from the preparation of one radiochemical compound to the preparation of another radiochemical compound. This only requires replacement or purification of the reaction vessel (or the reaction vessels) and the dosing units. Furthermore, in contrast to the prior art also hard-to-reach radiochemical compounds can be quickly synthesized because that only requires calling in the choice of another flow pattern into the control unit and performing it. This is put down to the fact that this only requires incorporation of additional reaction vessels and/or purifying modules. This is particularly advantageous in radiochemical compounds that can only be obtained by multi-stage reactions. The synthesis devices according to the prior art are practically limited to two stages and require costly designs if more than three stages are needed. Instead, the device according to the invention is particularly suitable for example for nucleophilic preparation of $^{18}$F-DOPA (6-[$^{18}$F]-fluoro-L-3,4-dihydroxyphenylalanine) which, as is well known, requires a three-stage reaction.

Preferably, a reaction module comprises several reaction vessels if the preparation of a predetermined radiochemical compound requires a multi-stage method. Preferably, several reaction modules are provided when different radiochemical compounds are to be prepared sequentially or in parallel by means of the device according to the invention.

The device according to the invention avoids the difficulties associated with the micro-fluidics of known miniaturized synthesis devices for radiochemical compounds. This is in particular put down to the flexible control of the pipetting heads in taking up and releasing educts and solvents, whereas taking up and releasing educts and solvents in micro-fluidal systems always depends strictly linear on a flow chart. The device according to the invention is dimensioned such that it can be used in a "standard hot cell". By "standard hot cell" a room is understood that is separated from its environment by shielding walls. The shielding walls typically consist of a material opaque to gamma radiation, for example lead plates. For example, the device can be used in a hot cell the interior of which has dimensions of 1 m×1 m×1 m or less.

A further advantage of the device according to the invention is that the preparation of one or more radiochemical compound(s) can be made without an operator intervention. For that, the substances needed for the preparation of a predetermined radiochemical compound are combined in kits. Here, each kit can be a storage module of the device according to the invention. The substances needed for the preparation of a predetermined radiochemical compound and which contain a radioisotope are preferably not provided in the kits, but in a separate storage module.

Said kits can be pre-conditioned such that the device according to the invention only needs to be instrumented with the kits to prepare the predetermined radiochemical compound. Instrumentation of the device according to the invention with the components of a kit can be done with respect to instrumentation plans with different instrumentation plans being provided for different radiochemical compounds, for example instrumentation plan 1 for a first tracer, tracer A, instrumentation plan 2 for a second tracer, tracer B, instrumentation plan 3 for a third tracer, tracer C etc. The instrumentation plan is sent to the user of the device according to the invention together with the kit.

The kit can also comprise a support plate, for example a micro-well plate. The support plate has reservoirs in which the substances are contained. Then, the support plate has only to be positioned at a given site of the storage module. In the following, the support plate is also referred to as kit plate. The kits can be disposable kits.

In addition to substances needed for the preparation of a predetermined radiochemical compound the kit can also contain cartridges and/or further purifying elements required for the separation of the prepared radiochemical compound from the reaction mixture. The user can introduce these cartridges and/or purifying elements into the purifying module. The instrumentation of the purifying module with the cartridges and/or purifying elements can be done in accordance with the guidelines of the instrumentation plan, i.e. the instrumentation plan not only includes places at which the required substances are positioned in the storage module, but also places at which the cartridges and/or purifying elements are positioned in the purifying module. Thus, the storage module and the purifying module of the device according to the invention are integrated in the kit.

If the user of the device according to the invention wants to prepare a certain radiochemical compound, for example tracer A, so it is provided with one or more kits containing the required substances and cartridges and/or purification means. Then, the user instruments the device according to the invention with the kit on which the required substances, cartridges and, if provided, further purification means are provided. Subsequently, by the software of a control module (described below) it instructs the device to prepare tracer A and starts the preparation method by entering the corresponding instruction. Then, the preparation of tracer A takes place fully automatically, interventions of the user are not required. If several radiochemical substances should be prepared simultaneously and/or in parallel the user also carries out the instrumentation with the kit required for the respective substance and enters the required instructions via the software of the control module. Then, all the radiochemical substances are prepared fully automatic. This is associated with a significant time saving.

Preparation of several radiochemical compounds can be in parallel and/or sequentially. The preparation of several radiochemical compounds in parallel requires several reaction modules.

Preferably, the reaction module has a heating and/or cooling facility. Suitably, the heating and/or cooling facility is arranged under the bottom of the reaction vessel or forms a jacket around the reaction vessel. Also a microwave can be used to heat the reaction vessel.

Preferably, the reaction vessel has a closure with the opening of the reaction vessel being opened when a substance needed for the preparation of the respective radiochemical compound is introduced into the reaction vessel or the reaction mixture or a part thereof is drained off from the reaction vessel and the opening is closed by means of the closure upon completion of supplying or draining off the substance. During labeling or hydrolysis of the radiochemical compound the reaction vessel is often closed and in this time, the dosing module is available for further functions.

Preferably, the closure of an opening of a reaction vessel is gastight. By means of the closure the opening can suitably be opened and closed automatically. This can also be done with the control unit.

Preferably, the reaction vessel is supported in the reaction module such that it can be set vibrating by means of the dosing unit introduced into the reaction vessel. In this way, thorough mixing of the reaction mixture in the reaction vessel can be achieved. Alternatively, to this end the reaction vessel can be attached on a moveable support member such that the reaction vessel can be set into a shaking movement. The support member is formed in the reaction module and can contain the heating and/or cooling facility. Also, an ultrasonic mixer or magnetic stirrer can be arranged in the reaction module.

Each pipetting head is movable relative to the storage module and the reaction module with the storage and reaction modules suitably being fixed.

Each pipetting head of the dosing module can be moved in x, y, and z directions. The motion of the pipetting head is controlled by a control module that is preferably arranged in the dosing module and can be controlled by a software. With the software it can be set when the pipetting head performs which motion. It is further determined with the software which volumes of the substances needed for the preparation of the radiochemical compound are taken up and released by the dosing units of the respective pipetting head.

If the dosing module has two pipetting heads so these pipetting heads preferably can be moved independently of each other. The advantage of two pipetting heads is that a substance passed through the purifying module can be directly taken and processed with a dosing unit carried by the second pipetting head which makes an additional storage vessel unnecessary.

Here, a dosing unit is meant to be a facility with an internal volume into which a given amount of a required substance or the reaction mixture can be received, in which the received amount of the required substance or the reaction mixture can be transported and from which the received amount of the required substance or the reaction mixture can be released. Receipt and release of the substance or the reaction mixture by the dosing unit is controlled by the control unit. For that, valves or actuators can be provided on the dosing unit that can be controlled by means of engines, pumps, vacuum, or a compressed gas such as compressed air. The facilities required for controlling the valves and actuators can be part of the dosing unit. For releasing and receiving substances the dosing unit has preferably a dosing syringe. As the dosing syringe active tips e.g. piezoelectrically driven micropipettes for dosing pico to nanoliter quantities or passive steel or polymer tips for dosing micro to milliliter quantities can be employed. Dosing units for liquids with active and passive dosing syringe enable reproducible and repetitive addressing of single quantities with a volume of 20 picoliter±10% where there are not upper limits.

In one embodiment, the dosing unit can comprise a fluidically closed cycle of at least one reservoir for system liquids such as deionized water, at least one pump, at least one valve and at least one dosing syringe. As is typical for syringe pumps the pump and the valve can be connected to one system. Alternatively, there can also be provided other pump-valve arrangements. The fluidically closed cycle can be realized by means of pipelines, for example by a tube.

A dosing module can have different dosing units, in particular dosing units with a different construction adapted to the given transport function.

For taking up, transportation and releasing liquids there can be used dosing units with dosing syringes. Taking up the given amount of the required substance or the reaction mixture into the internal volume, the occlusion of the amount in the internal volume for transportation, and release of the amount from the internal volume are controlled by means of syringe pumps.

For the take-up, transportation and release of solids the pipetting head can carry a dosing unit which can take up a powdered substance from the storage module, transport it to the reaction module and introduce it into a reaction vessel of the reaction module via the opening.

In one embodiment of the invention the pipetting head carries a dosing unit which can take up a powdered substance from the storage module, transport it to the reaction module and introduce it into a reaction vessel of the reaction module via the opening, and at least one further dosing unit which can take up a liquid substance from the storage module, transport it to the reaction module and introduce it into a reaction vessel of the reaction module via the opening. The dosing unit which can take up a liquid substance from the storage module, transport it to the reaction module and introduce it into a reaction vessel of the reaction module via the opening can also be used to take up the reaction mixture or a part of that from the reaction vessel, transport it and release it at a given place.

Herein, the term "liquid" or "liquid substance" is also intended to comprise solutions and dispersions of substances in a solvent. It is also intended to comprise the reaction mixture.

Moreover, a dosing unit should have a first channel for supplying a gas such as nitrogen into the reaction vessel and a second channel for draining off gaseous reaction products from the reaction vessel. Here, the first channel may simultaneously serve to take up, transport and release a required substance or the reaction mixture or a part of that. Here, the first channel is formed such that it penetrates the reaction vessel deeper than the second channel. Dosing units are designated according to the number of channels as single lumen, double lumen, triple lumen etc. dosing units. A triple lumen dosing unit can have for example a first channel for the take-up, transport and release of a substance needed for the synthesis of the radiochemical compound, a second channel for supplying a gas into a reaction vessel and a third channel for draining off gaseous reaction products from the reaction vessel. For that, a vacuum can be applied to the third channel.

By means of the dosing units liquids and solids can be exactly dosed. The dosing units preferably have an internal volume of 10 to 5000 µl, more preferably 50 to 1,000 µl.

The device according to the invention enables the use of solids for the preparation of predetermined radiochemical compounds, in other words, the required substances can be present as solids. That relates in particular to precursor compounds and catalysts. Solids are preferably used if a longer storage results in malfunction, e.g. decomposition of the substance. Solid dosing according to the invention enables dosing of a few µg mass quantities. For the dosage of solids dosing units adapted to this purpose are provided which in the following are referred to as solid pipette. The advantage of a solid pipette is the combination of a relatively exact dosage and in particular easier stocking of the substance in the stable dry state. The storage module of a kit with solid stock is basically other than a stock for liquids. The solids can be laced with a solvent in the dosing unit immediately before they are used if the substances for the preparation of the radiochemical compound must be in solution. The use of solids in the dosing units and the kits avoids problems that are put down to the insufficient stability of solutions of these solids. This will increase the durability of the kits. It is particularly advantageous that the device according to the invention enables the employment of powdered catalysts. This will significantly expand the number of radiochemical compounds that can be prepared by means of the device according to the invention.

Finally, a dosing unit can be provided which can apply liquids on one end of a purification cartridge, press it through the purification cartridge and take it up again on the other end of the purification cartridge. For that, such a dosing unit has a first channel with an opening that can be contacted with the entry of the purification cartridge such that a liquid can be introduced from the first channel into the purification cartridge. Furthermore, the dosing unit has a second channel with an opening that is in contact with the exit of the purification cartridge when the opening of the first channel is in contact with the entry of the purification cartridge. By means of pressure applied to the liquid via the first channel the liquid is pressed into the purification cartridge and through it via the exit of the purification cartridge into the second channel. When passing the purification cartridge the liquid is purified. Then, the purified liquid is in the second channel.

Suitably, the storage module comprises reservoirs for all the required substances. Preferably, each reservoir has a volume of 10 to 20,000 µl, more preferably 50 to 5,000 µl. Preferably, the storage module has a separate reservoir for a powdered substance.

In one embodiment of invention one or more storage modules are stored in a microplate stacker. This is in particular advantageous when the storage modules are present as kits that comprise kit plates.

Optionally, the microplate stacker may have facilities for controlling the temperature and/or the humidity and/or $CO_2$ concentration. A stacker is a rack wherein several kits are present stacked with all of the substances and purification cartridges. The microplate stacker and/or a storage module have a transportation facility, e.g. a gripper or a conveyor band, which takes up the kit required for the preparation of a predetermined radiochemical compound from of the rack and puts it down at a given place within the device according to the invention. After that, the dosing units have access to the substances of the kit. Each kit, suitably the kit plate, can have an individual address realized for example in the form of a transponder chip or a barcode by which a confusion of kits can be avoided. In this way it is possible to instrument the device with one or more kits for the synthesis of different or equal radiochemical substances, which may be a significant gain in time. Each movement of the kit plate from the stacker to the synthesis station and back is effected via the control unit of the same.

The dosing units transport the given amount of the required substances at the prescribed time from the reservoirs of the storage module into the reaction vessel. If several dosing units are provided then it is also prescribed which of the dosing units at which time takes up which required substance and transfers it to the reaction vessel. The specifications are stored by means of software in the control unit which then controls the pipetting head via the robotics. Also, the dosing unit can be used to take up the reaction mixture or a part thereof from the reaction vessel and transport it to a given place, for example the inlet of the purification module, for example a HPLC. As a rule, the reaction mixture is taken up from the reaction vessel after reaction of the required substances and contains the desired radiochemical compound which is then purified in the purification module. After completion of the purification the purified radiochemical compound can be transferred to the filling cell. Preferably, the filling cell is a part of the device according to the invention.

The term "radiochemical compound" is intended to comprise all organic or inorganic compounds having a radioisotope. In particular, the term "radiochemical compound" comprises radiochemical medicinal drugs and diagnostic reagents, particularly preferred radiotracers, radiopharmaceutical agents, and radioligands.

Preferred radioisotopes are $^{68}$Ga, $^{90}$Y, $^{99}$Tc, $^{111}$In, $^{64}$Cu, Lu$^{177}$, $^{11}$C, $^{18}$F, $^{124}$I, $^{13}$N, and $^{15}$O, more preferably $^{11}$C, $^{18}$F, and $^{124}$I and particularly preferred $^{18}$F.

Preferred $^{18}$F labeled radiotracers are 2-deoxy-2-[$^{18}$F]fluoro-D-glucose ([$^{18}$F]-FDG), 6-[$^{18}$F]fluoro-L-3,4-dihydroxyphenylalanine ([$^{18}$F]-FDOPA), 6-[$^{18}$F]fluoro-L-metatyrosine ([$^{18}$F]-FMT), [$^{18}$F]fluorocholine, [$^{18}$F] fluoroethylcholine, 9-[4-[$^{18}$F]fluoro-3-(hydroxymethyl)butyl]guanine ([$^{18}$F]-FHBG), 9-[(3-[$^{18}$F]fluoro-1-hydroxy-2-propoxy)methyl]guanine ([$^{18}$F]-FHPG), 3-(2'-[$^{18}$F]fluoroethyl)spiperone ([$^{18}$F]-FESP), 3'-deoxy-3'-[$^{18}$F]fluorothymidine ([$^{18}$F]-FLT), 4-[$^{18}$F]fluoro-N-[2-[1-(2-methoxyphenyl)-1-piperazinyl]ethyl]-N-2-pyridinyl-benzamide ([$^{18}$F]-p-MPPF), 2-(1-{6-[(2-[$^{18}$F]fluoroethyl)(methyl)amino]-2-naphthyl}ethylidine)malonitrile ([$^{18}$F]-FDDNP), 2-[$^{18}$F]fluoro-α-methyltyrosine, [$^{18}$F]fluoromisonidazole ([$^{18}$F]-FMISO), and 5-[$^{18}$F]fluoro-2'-deoxyuridine ([$^{18}$F]-FdUrd).

According to the invention there is further provided a method for the preparation of radiochemical compounds by means of the device according to the invention wherein by means of dosing units the substances required for the preparation of the respective radiochemical compound are introduced into a reaction vessel of the reaction module and wherein the dosing units can be moved by a pipetting head in x, y directions or in x, y, and z directions.

Preferably, for this purpose substances required for the preparation of the respective radiochemical compound are sequentially introduced into the reaction vessel of the reaction module. For that, several dosing units can be used wherein the same dosing unit can be used to introduced several substances. In this case, the dosing unit should be rinsed in a washing station after supplying a first substance and taking up a second substance.

Advantageously, the prepared radiochemical compound can also be taken up from the reaction vessel by means of a dosing unit. Said dosing unit can be one of the dosing units that have already been used for the introduction of the substance into the reaction vessel. Preferably, said dosing unit has been rinsed in the washing station before. After taking up from the reaction vessel the prepared radiochemical compound can be transferred to a purification module by means of the dosing unit.

In one embodiment the method according to the invention comprises the following steps:
(a) introducing a solution of a radioactive isotope into the reaction vessel;
(b) drying a radioactive isotope;
(c) introducing a precursor compound of the radiochemical compound to be prepared into the reaction vessel;
(d) reacting the precursor compound with the radioactive isotope;
(e) taking up the prepared radiochemical compound from the reaction vessel;
(f) purifying the prepared radiochemical compound by means of one or more cartridges and/or by means of HPLC; and
(g) dispersing the prepared radiochemical compound with a buffer or NaCl-containing solution as well as filling into ready-made vials.

In step (a) the solution of the radioactive isotope is suitably an aqueous solution.

In step (c) the precursor compound is preferably introduced as solid or dissolved in an organic solvent into the reaction vessel. When the precursor compound is to be introduced as a solution so the precursor compound immediately before introduction into the reaction vessel can be laced with an organic solvent or already be provided in the dissolved form. When using a kit with a kit plate the solution can already be present in the kit or else, a solvent is transferred by means of a dosing unit into the solid vial present on the kit plate in which the undissolved precursor compound is present.

Following step (d) and before step (e) it can be provided that one or more protective group(s) having the precursor group is/are cleaved off from the reaction mixture obtained in step (d). For example, this is done by hydrolysis.

The device according to the invention is particularly suitable for the preparation of radiotracers, radiopharmaceutical agents, and radioligands.

Precursor compounds are also referred to as precursors. The term "precursor compound" or "precursor" comprises organic or inorganic compounds reacting with a radioisotope to obtain a radiochemical compound. Examples of precursor compounds are amino acids, nucleosides, nucleotides, proteins, sugar, and derivative of these compounds. Specific examples are 1,3,4,6-tetra-O-acetyl-2-O-trifluoromethanesulfonyl-beta-D-mannopyranose for the preparation of [$^{18}$F]-FDG; N$^2$-(p-anisyldiphenylmethyl)-9-[(4-p-toluenesulfonyloxy)-3-(p-anisyldiphenylmethoxymethyl)butyl]guanine for the preparation of [$^{18}$F]-FHBG; N$^2$-(p-anisyldiphenylmethyl)-9-[[1-(p-anisyldiphenylmethoxy)-3-(p-toluenesulfonyloxy)-2-propoxy]methyl]guanine for the preparation of [$^{18}$F]-FHPG; 8-[4-(4-fluorophenyl)-4,4-(ethylenedioxy)butyl]-3-[2'-(2,4,6-trimethylphenylsulfonyloxyethyl)]-1-phenyl-1,3,8-triazaspiro[4.5]decane-4-one for the preparation of [$^{18}$F]-FESP; 5'-O-boc-2,3'-anhydrothymidine, or N-boc-5'-O-dimethoxytrityl-3'-O-(4-nitrophenylsulfonyl)thymidine for the preparation of [$^{18}$F]-FLT; N-[2-[4-(2-methoxyphenyl)-1-piperazinyl]ethyl]-4-nitro-N-2-pyridinyl-1-benzamide for the preparation of [$^{18}$F]-p-MPPF; 2-(1-{6-[(2-(p-toluenesulfonyloxy)ethyl)(methyl)amino]-2-naphthyl}ethylidine)malonitrile for the preparation of [$^{18}$F]-FDDNP; 1,2-bis(tosyloxy)ethane, and N,N-dimethylethanolamine for the preparation of [$^{18}$F]fluoroethylcholine; and ditosylmethane or dibromomethane on the one hand and N,N-dimethylethanolamine on the other hand for the preparation of [$^{18}$F]-fluorocholine.

The precursor compound often contains protective groups to protect functional groups that should not react with the radioactive isotope. Following step (c) and prior to the execution of step (d) the protective groups are preferably cleaved from the reaction product obtained in step (c).

By the term "radiotracer" in the present invention an artificial, radio-labeled, endogenous or exogenous substance is understood participating in metabolism after having been introduced into the living body and moreover, enables or facilitates various examinations.

By the term "radioligand" in the present invention a substance labeled with a radionuclide is understood which as a ligand can bind to a target protein, for example to a receptor.

According to the invention there is further provided a kit comprising
(i) a support plate with reservoirs for receiving substances required for the preparation of a radiochemical compound,
(ii) one or more cartridges for purification of the substances and/or the radiochemical compound as well as
(iii) substances required for the preparation of a radiochemical compound.

The kit can comprise further constituents, in particular the constituents described above in context with the kit.

In the following, the invention is explained in more detail with the help of examples not intended to limit the invention with respect to the drawings. Here.

EXAMPLE 1

Figure 1:
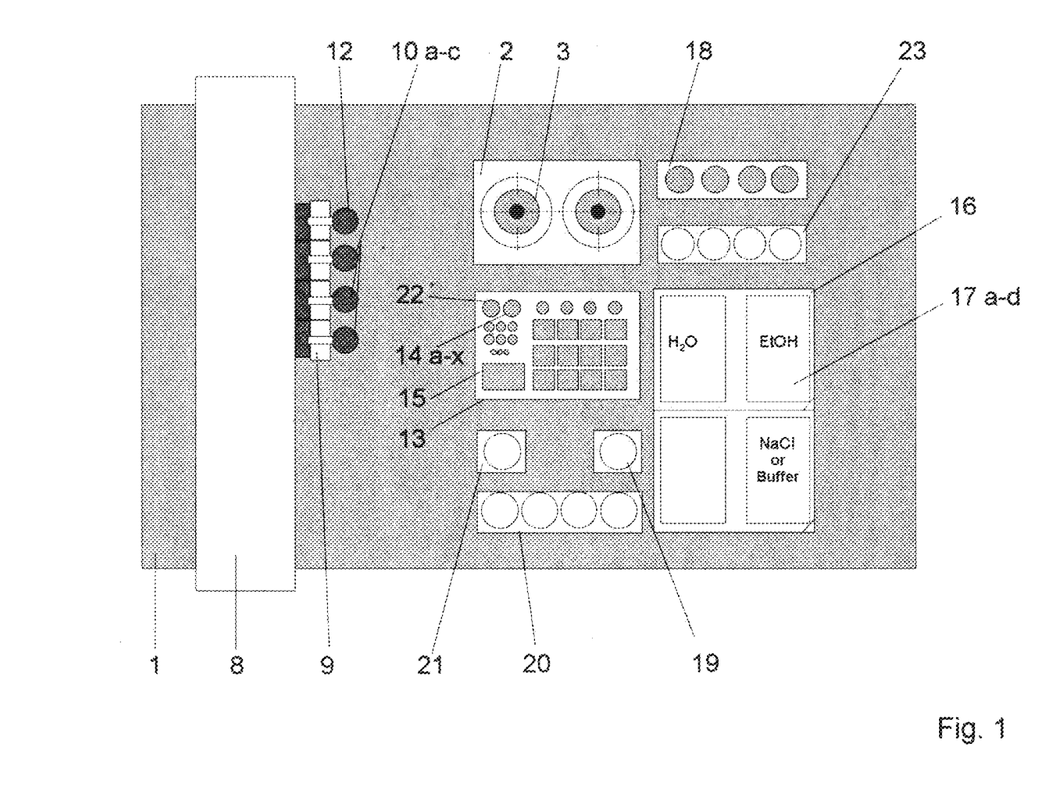
FIG. 1 shows a schematic representation of an embodiment of the device according to the invention.

The synthesis device 1 according to the invention schematically shown in FIG. 1 has a reaction module 2 with two reaction vessels 3. Each reaction vessel 3 is arranged within a housing 4 which is open at the top. In the housing 4 a cooling and/or heating facility 5 is arranged (see, FIG. 2a). The synthesis device 1 can be arranged in a hot cell 24, as shown in FIG. 3.

Figure 2A:
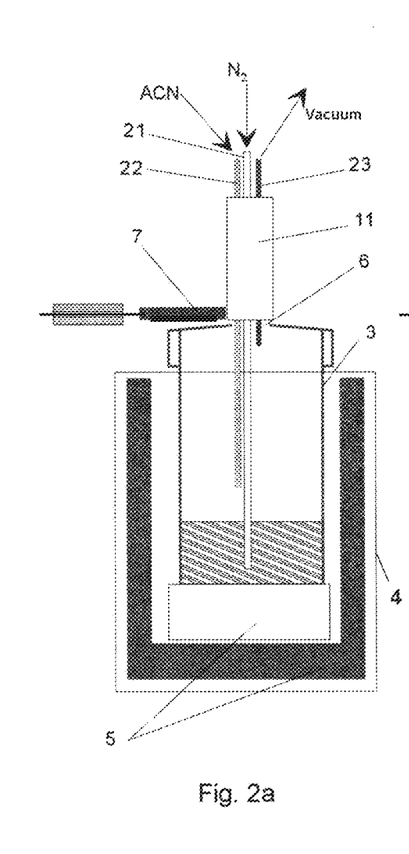
FIG. 2a shows a schematic sectional view of the reaction module and a dosing unit having three channels the pipetting tip of which is introduced into the reaction vessel.
Figure 2B:
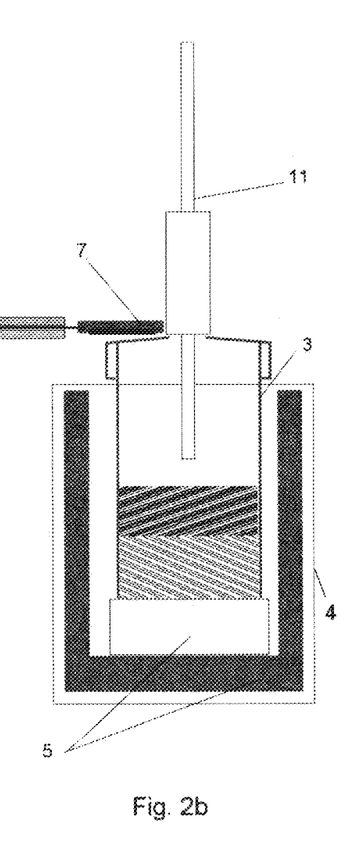
FIG. 2b shows a schematic sectional view of the reaction module and a dosing unit the pipetting tip of which is introduced into the reaction vessel.
Figure 2C:
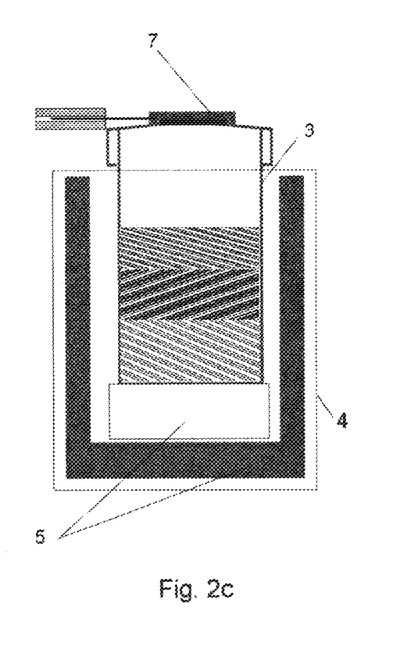
FIG. 2c shows a schematic sectional view of the reaction module with the reactor being closed during a reaction.
Figure 3:
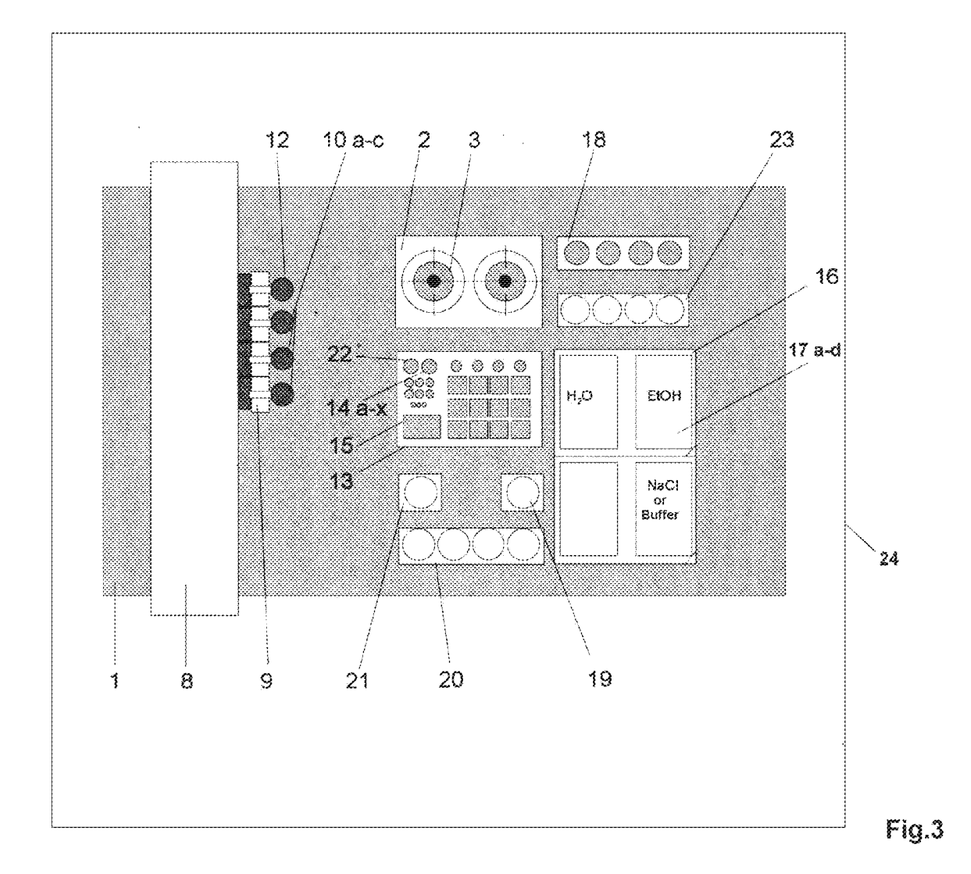
FIG. 3 shows a schematic representation of the embodiment of the device according to the invention shown in FIG. 1 inserted into a hot cell.

As can be seen in FIG. 2a, the reaction vessel 3 is a substantially cylindrical container having an opening 6 at its top through which substances can be introduced into and removed from the reaction vessel 3. Opening 6 of the reaction vessel 3 is closed with closure 7 if no substances are introduced into or removed from the reaction vessel 3.

According to FIG. 1, the device 1 further has a dosing module 8. The dosing module 8 comprises a pipetting head 9 which can be moved relatively and channel-selectively in the z-axis to the reaction vessel by means of a robotics which is part of the dosing module 8. In the embodiment shown in FIG. 1 the pipetting head 9 can be moved as a whole in the x, y-axis with the x and y-axis lying in the plane of the page whereas the z-axis runs vertically to the plane of the page. The motion of the pipetting head 9 is controlled by a software. The robotics is controlled by a control module (not shown).

In FIG. 1 the pipetting head 9 carries four dosing units 10a, 10b, 10c, and 12. Of course, the number of dosing units can be smaller or greater than four as long as at least one dosing unit is provided. A dosing unit 10 is a facility which can take-up, transport and release a substance. In FIG. 1 the pipetting head 3 carried the following dosing units: three dosing syringes 11 and one powder pipette 12. Each of the dosing syringes 11 is connected to a syringe pump arranged in the dosing module 8. The powder pipette 12 is connected to a vacuum-compressed air unit arranged in the dosing module 8. By means of the syringe pump and the vacuum-compressed air unit of the dosing module 8 take-up and release of a substance by the dosing units 10 is controlled.

At least one of the dosing syringes 11 (for example dosing syringe 11b of the dosing unit 10b) has two channels for taking-up, transporting and releasing a substance required for the synthesis of the radiochemical compound as well as for supplying a gas into the reaction module and a third channel for draining off gaseous reaction products. For that, a vacuum can be applied to the third channel. Via the first channel, for example acetonitrile (ACN) or a solution of acetonitrile can be supplied, transported and drained off. Via the second channel, for example nitrogen can be supplied.

Furthermore, device 1 comprises a storage module 13 containing a storage vessel 14 for the substances needed for the synthesis of the desired radiochemical compound. In the embodiment shown in FIG. 1 two types of storage vessels 14 are provided, a storage vessel 15 for receiving a powdered substance (for example Mannose Triflate, as shown in example 2) and a storage module 16 for receiving liquids. The storage module 16 can comprise several reservoirs 17 for receiving various liquids. The number of reservoirs 17 should correspond to the number of liquid substances needed for the synthesis of the radiochemical compound or should be greater than that. FIG. 1 shows a storage module 16 with six reservoirs 17.

FIG. 1 shows a washing station 18 which can be formed separately from the storage module 13. The washing station 18 has reservoirs containing purification substances for the dosing units 10.

The mode of operation of the device shown in FIG. 1 is described in example 2 below with respect to the preparation of [$^{18}$F]-FDG.

EXAMPLE 2

Synthesis of [$^{18}$F]-FDG

In the following the synthesis of [$^{18}$F]-FDG using the device illustrated in FIG. 1 is described.

Basic Principles of the Preparation of [$^{18}$F]-FDG

As precursor for the preparation of [$^{18}$F]-FDG there is used anhydrous 1,3,4,6-tetra-O-acetyl-2-O-trifluoromethane-sulfonyl-beta-D-mannopyranose (also known as Mannose Triflate or TATM). Fluorination of the precursor is done by introducing $^{18}$F by means of nucleophilic substitution to give 2-[$^{18}$F]fluoro-1,3,4,6-tetra-O-acetyl-D-glucose in acetonitrile under nitrogen atmosphere. Subsequently, the protective groups are removed by basic hydrolysis. The basic hydrolysis is typically performed with sodium hydroxide solution at temperatures of 80° C. Subsequently, the reaction solution is neutralized with hydrochloric acid and then diluted with water.

The thus obtained crude product is purified by means of liquid chromatography, for example using a purification cartridge to give [$^{18}$F]-FDG. More details on the preparation of [$^{18}$F]-FDG are described in Coenen H. H. et al., Recommendation for a practical production of 2-[$^{18}$F]Fluoro-2-Desoxy-D-Glucose. Appl. Radiat. Isot. (38) 1997, 605-610.

Starting Materials

For the Preparation of [$^{18}$F]-FDG by means of the device shown in FIG. 1 the following substances are needed as starting materials. There are also given the place of provision in device 1 prior to the start of synthesis and the amount provided. Both the place and also the amount are only exemplary.

(1) Mannose Triflate: powdered; reservoir 15 of storage vessel 13; 20 mg
(2) [$^{18}$F] fluoride: half-life 110 min; in aqueous solution 1.2 ml, in reservoir 19

(3) Eluent Solution consisting of: 22 mg Kryptofix™ 2.2.2, 7 mg potassium carbonate in 750 µl water/acetonitrile (volume ratio 1/1); reservoir 14a of storage module 13;
(4) Ethanol, 200 µl, second reservoir 14b of storage module 13
(5) sodium hydroxide: 0.2M aqueous solution; reservoir 14c of storage module 13; 200 µl
(6) hydrochloric acid: 0.2M aqueous solution; reservoir 14d of storage module 13; 200 µl
(5) water, reservoir 17a of storage module 16; 15 ml
(6) acetonitrile, reservoir 14e of storage module 13, 1 ml
(7) Citrate buffer solution, consisting of: 25.2 mg Di-sodium-hydrogen-citrate-1,5-hydrate, 144.4 mg Tri-sodium-citrate-2-hydrate, 86.9 mg sodium chloride, 2.9 ml water for injection purposes; 0.1 ml hydrochloric acid (2 M), reservoir 14f von storage module 13,
(8) 0.9% NaCl solution, reservoir 17c of storage module 16

Storage module 13 and storage module 16 each are preconditioned kits. Both kits comprise a kit plate. Storage module 13 further comprises a QMA cartridge for separating the enriched water from the [$^{18}$F] fluoride. Storage module 16 comprises substances needed in most of the methods for the preparation of radiochemical compounds, whereas storage module 13 comprises substances specifically needed for the preparation of the predetermined radiochemical compound. The aqueous [$^{18}$F] fluoride solution is placed in a separate storage module.

Step 1

Dosing module 8 moves the pipetting head 9 with the first dosing syringe 11a toward storage vessel 19. By means of the syringe pump 1.2 ml of [$^{18}$F] fluoride are taken up by the dosing syringe 11a. Then, the pipetting head 9 moves the dosing syringe 11a containing the [$^{18}$F] fluoride to the storage module 13 present as kit and having the QMA cartridge and applies the [$^{18}$F] fluoride to the QMA cartridge. The passing aqueous solution is taken up with a dosing syringe 11c of the dosing unit 10b and released in the storage vessel 21. The eluent solution of the storage module 13 (kit) is taken up with the dosing syringe 11a and applied to the QMA cartridge. The passing eluent solution with the [$^{18}$F] fluoride is taken up by the second dosing syringe 11b of the second dosing unit 10b and filled into the reaction vessel 3.

Step 2

Following step 1 the dosing module 8 moves the pipetting head 9 with the second dosing syringe 11b to the reaction vessel 3. Dosing syringe 11b is a triple lumen dosing syringe with a first internal channel 21 for supplying nitrogen, a second internal channel for adding acetonitrile for azeotropic drying and a third internal channel for vacuum suction. The channel for vacuum suction 23 serves to drain off the supplied nitrogen and optional waste products. During introduction of the pipetting tip of the dosing syringe 11b into the reaction vessel 3 the closure 7 of opening 6 of the reaction vessel 3 is opened, at this moment the penetrating dosing syringe 11 hermetically seals opening 6 of the reaction vessel 3. After penetration of the dosing syringe 11b alternately nitrogen and acetonitrile is introduced via channel 21 and channel 22 into the reaction vessel 3 and in this way, an azeotropic drying is realized. By means of the cooling and heating facility 5 the temperature of the eluent mixture contained in the reaction vessel 3 is increased to 95° C. The supplied nitrogen, the water, and the acetonitrile are removed from the reaction vessel 3 by means of the second channel 23 under vacuum of the dosing syringe 11b. Upon completion of drying the dosing syringe 11b is removed from the reaction vessel 3 with the opening 6 of the reaction vessel 3 being closed by the closure 7.

Step 3

The dosing module 8 moves the pipetting head 9 with the powder pipette 12 from its initial position to storage vessel 15 for powdered substances. Powder pipette 12 takes up 20 mg of Mannose Triflate from storage vessel 15 by means of a vacuum-compressed air unit. Then, pipetting head 9 moves the powder pipette 12 containing the Mannose Triflate to an empty vial 22 placed on the storage module 13 (kit). After penetration of the dosing syringe of the powder pipette 12 the release of the Mannose Triflate into the empty vial 22 is effected by the vacuum-compressed air unit. The dosing module 8 moves the pipetting head 9 with the first dosing syringe 11a to the second reservoir 14 in the storage module 13. By means of the syringe pump 1000 µl of acetonitrile are taken up by the dosing syringe 11a and are moved to vial 22 to dissolve the 20 mg of Mannose Triflate and take up the solution with the same dosing syringe 11a again. Subsequently, the pipetting head 9 moves the dosing syringe 11a containing the precursor solution to the reaction vessel 3. During introduction of the dosing syringe into the reaction vessel 3 closure 7 is removed from the opening 6 of the reaction vessel 3 with opening 6 being hermetically sealed by the penetrating dosing syringe. After penetration of the dosing syringe 11a release of the precursor solution into the reaction vessel 3 is effected by the syringe pump. During introduction of the dosing syringe 11a into the reaction vessel 3 closure 7 is removed from the opening 6 of the reaction vessel 3 with opening 6 being hermetically sealed by the penetrating dosing syringe. After penetration of the dosing syringe 11a release of the precursor solution into the reaction vessel 3 is effected by the syringe pump. By means of the cooling and heating facility 5 the temperature of the reaction mixture contained in the reaction vessel 3 in increased to 100° C. Then, dosing syringe 11a is removed from the reaction vessel 3 with opening 6 of the reaction vessel being closed by the closure 7. Then, the dosing module 8 moves the pipetting head 9 with the dosing syringe 11a to washing station 18 where the dosing syringe 11a is washed with acetone.

Step 4

After a reaction time of 5 min for evaporation of the acetonitrile nitrogen is introduced via channel 21 into the reaction vessel by the penetration of the triple lumen dosing syringe 11b into the closure of the reaction vial. After complete evaporation of the acetonitrile and cooling the reaction vessel down to 50° C. the dosing module 8 moves the pipetting head 9 with the first dosing syringe 11a to the second storage vessel 14 in the storage module 13. By means of the syringe pump 200 µl of ethanol are taken up by the dosing syringe 11a. Then, the pipetting head 9 moves the dosing syringe with the ethanol to the reaction vessel 3. During introduction of the pipetting tip of the dosing syringe 11a into the reaction vessel 3 closure 7 is removed from the opening 6 of the reaction vessel 3 with opening 6 being hermetically sealed by the penetrating dosing syringe. After penetration of the pipetting tip of the dosing syringe 11a release of the ethanol into the reaction vessel 3 is effected by the syringe pump. Then, the dosing module 8 moves the pipetting head 9 with the dosing syringe 11a to the washing station 18 where the dosing syringe 11a is washed with acetone.

Step 5

Then, the dosing module 8 moves the pipetting head 9 with the first dosing syringe 11a to the second storage vessel 14 in the storage module 13 (kit). By means of the syringe pump 500 µl of 2N sodium hydroxide solution are taken up by the dosing syringe 11a. Then, pipetting head 9 moves the dosing syringe 11a containing the sodium hydroxide solution to the reaction vessel 3. During introduction of the pipetting tip of the dosing syringe 11a into the reaction vessel 3 closure 7 is removed from the opening 6 of the reaction vessel 3 with opening 6 being hermetically sealed by the penetrating dosing syringe. After penetration of the pipetting tip of the dosing syringe 11a release of the sodium hydroxide solution into the reaction vessel 3 is effected by the syringe pump. By means of the cooling and heating facility 5 the temperature of the reaction mixture contained in the reaction vessel 3 in increased to 80° C. Then, dosing syringe 11a is removed from the reaction vessel 3 with opening 6 of the reaction vessel being closed by the closure 7. Then, the dosing module 8 moves the pipetting head 9 with the dosing syringe 11a to washing station 18 where the dosing syringe 11a is washed with acetone.

Step 6

After hydrolysis with a reaction time of 5 min dosing module 8 moves the pipetting head 9 with the first dosing syringe 11a to the third storage vessel in the storage module 13. By means of the syringe pump 500 μl of 2N hydrochloric acid are taken up by the dosing syringe 11a. Then, pipetting head 9 moves the dosing syringe 11a containing the hydrochloric acid to reaction vessel 3. The dosing syringe is introduced into the reaction vessel 3 as far as the temperature has reached room temperature by means of the cooling and heating facility 5 of the present reaction mixture there. During introduction of the dosing syringe 11a into the reaction vessel 3 closure 7 is removed from the opening 6 of the reaction vessel 3 with opening 6 being hermetically sealed by the penetrating pipetting tip. After penetration of the pipetting tip of the dosing syringe 11a release of the hydrochloric acid into the reaction vessel 3 is effected by the syringe pump. Then, dosing syringe 11a is removed from the reaction vessel 3 with opening 6 of the reaction vessel being closed by the closure 7. Then, the dosing module 8 moves the pipetting head 9 with the dosing syringe 11a to washing station 18 where the dosing syringe 11a is washed with acetone.

Step 7

Following step 6 the dosing module 8 moves the pipetting head 9 with the first dosing syringe 11a to the storage reservoir 17a in the storage module 16. By means of the syringe pump 15 ml of water are taken up by the dosing syringe 11. Then, pipetting head 9 moves the dosing syringe 11a containing the water to the reaction vessel 3. The dosing syringe is introduced into the reaction vessel 3. During introduction of the dosing syringe 11a into the reaction vessel 3 the closure 7 is removed from the opening 6 of the reaction vessel 3 with opening 6 being hermetically sealed by the penetrating dosing syringe. After penetration of the dosing syringe 11a 1 to 2 ml of water are filled into the reaction vessel by means of the syringe pump and immediately drawn back into the syringe pump such that the entire 15 ml of water and the reaction mixture are mixed in a reservoir of the syringe pump. Then, dosing syringe 11a is removed from the reaction vessel 3 with opening 6 of the reaction vessel being sealed by the closure 7. Then, the dosing module 8 moves the pipetting head 9 with the dosing syringe 11a to the kit 13 for purification (cartridge) and presses the whole aqueous solution with the radiotracer $^{18}$F-FDG over the cartridge. The passing aqueous solution is taken up by a second dosing syringe 11c of the dosing unit 10b and transported to the final vial 20 with a bacterial filter placed thereon. The aqueous solution is filled into the final vial 20 through the bacterial filter. The final vial 20 already contains a citrate buffer solution which has been filled in during hydrolysis of the radiotracer by the free dosing syringe 11a via the bacterial filter.

EXAMPLE 3

Example 3 corresponds to example 2 except that an additional step, step 8, is provided for fractionation of patient's doses.

Step 8

After purification of the dosing syringe 11a in the washing station the normal saline solution (0.9%) is removed from the storage vessel 17c and distributed among several vials with a bacterial filter placed thereon in position 23 on device 1. Then, the individual patient's doses can be removed from the final vial 20 with the dosing module 8 and distributed among the individual normal saline solutions by means of the dosing syringe 11a.

LIST OF REFERENCE MARKS

1 Device
2 Reaction Module
3 Reaction Vessel
4 Housing
5 Cooling and/or Heating Facility
6 Opening of the Reaction Vessel
7 Closure of the Reaction Vessel
8 Dosing Module
9 Pipetting Head
10 Dosing Units
11 Dosing Syringes
12 Powder Pipette
13 Kit/Storage Module
14 Storage Vessel for Chemicals to be used
15 Storage Vessel for powdered Substances
16 Storage Module for liquid Substances
17 Reservoirs in the Storage Module 16
18 Washing Station
19 Fluoride Reservoir
20 Final Vial
21 $^{18}$O Water
22 Empty Vial
23 Vials for Patient's Doses
24 Hot Cell

The invention claimed is:

1. A device for the preparation of radiochemical compounds comprising:
at least a reaction module, a dosing module, and a storage module, wherein
the reaction module has at least one reaction vessel having a closable opening through which substances needed for the preparation of a predetermined radiochemical compound can be introduced into the reaction vessel of the reaction module and through which the prepared radiochemical compound can be removed from the reaction vessel of the reaction module;
the dosing module has at least one pipetting head which can be moved relative to the storage module and the reaction module and in x, y, and z directions and also has one or more dosing units, wherein at least one dosing unit is a triple lumen dosing unit having a first channel for taking up, transporting, and releasing a substance needed for the synthesis of the radio-chemical compound, a second channel for supplying a gas into a reaction vessel and a third channel for draining off gaseous reaction products from the reaction vessel; and
at least one reservoir for one of the substances needed for the preparation of the respective radiochemical compound is formed in the storage module;

wherein purification means required for the separation of the prepared radiochemical compound from the reaction mixture are integrated into the storage module; and wherein the reaction module, the dosing module, and the storage module are arranged in a hot cell.

2. The device according to claim 1, wherein the reaction vessel of the reaction module has an internal volume of 10 nl to 20,000 µl.

3. The device according to claim 1, wherein the reaction module has a heating facility or cooling facility or microwave.

4. The device according to claim 1, wherein the reaction vessel has a closure with the opening being opened when a substance needed for the preparation of the respective radiochemical compound is introduced into the reaction vessel or the reaction mixture or a part of that is drained off from the reaction vessel and the opening being closed by means of the closure upon completion of supplying or draining off the substance.

5. The device according to claim 4, wherein the dosing unit seals the opening while the substance needed for the preparation of the respective radiochemical compound is introduced into the reaction vessel or the reaction mixture or a part of that is drained off from the reaction vessel.

6. The device according to claim 1, wherein it has at least one dosing unit which can take up a powdered substance from the storage module, transport it to the reaction module and introduce it into the reaction vessel via the opening, or at least one further dosing unit which can take up a liquid substance from the storage module, transport it to the reaction module and introduce it into the reaction vessel via the opening.

7. The device according to claim 1, wherein at least one dosing unit has two or more channels for supplying or draining off liquid and gaseous substances from a reaction vessel.

8. The device according to claim 1, wherein the dosing unit has two pipetting heads which are moveable independently of each other.

9. The device according to claim 1, wherein it further comprises a dispensing module for the prepared radiochemical compound.

* * * * *